United States Patent
Kamekawa et al.

(10) Patent No.: US 7,977,496 B2
(45) Date of Patent: Jul. 12, 2011

(54) PROCESS FOR PRODUCING NITROGUANIDINE DERIVATIVES

(75) Inventors: Hisato Kamekawa, Omuta (JP);
Tomotaka Miyashita, Kawasaki (JP);
Hiroyuki Katsuta, Chiba (JP); Toshio Kitashima, Omuta (JP)

(73) Assignee: Mitsui Chemicals, Inc., Minato-Ku, Tokyo (JP)

( * ) Notice: Subject to any disclaimer, the term of this patent is extended or adjusted under 35 U.S.C. 154(b) by 0 days.

(21) Appl. No.: 12/278,497

(22) PCT Filed: Feb. 7, 2007

(86) PCT No.: PCT/JP2007/000066
§ 371 (c)(1),
(2), (4) Date: Aug. 6, 2008

(87) PCT Pub. No.: WO2007/091391
PCT Pub. Date: Aug. 16, 2007

(65) Prior Publication Data
US 2009/0176990 A1    Jul. 9, 2009

(30) Foreign Application Priority Data
Feb. 10, 2006   (JP) ................. 2006-033941

(51) Int. Cl.
*C07D 307/02* (2006.01)
*C07D 213/56* (2006.01)
(52) U.S. Cl. .................... 549/491; 546/338
(58) Field of Classification Search ........... 549/491; 546/338
See application file for complete search history.

(56) References Cited

U.S. PATENT DOCUMENTS

| 242,003 | A | * | 5/1881 | Tanner et al. ............... 294/15 |
| 2,424,003 | A | * | 7/1947 | Tanner, Jr. et al. ............ 435/66 |
| 6,124,466 | A | * | 9/2000 | Matsuno et al. .............. 546/332 |

FOREIGN PATENT DOCUMENTS

| EP | 0 974 579 A1 | 1/2000 |
| JP | 2-288860 A | 11/1990 |
| JP | 3-157308 A | 7/1991 |
| JP | 3-291267 A | 12/1991 |
| JP | 7-179448 A | 7/1995 |
| JP | 10-120666 A | 5/1998 |
| JP | 2000-103776 A | 4/2000 |

OTHER PUBLICATIONS

Form PCT/ISA/210 (International Search Report) dated May 1, 2007.
Extended Search Report issued on Sep. 22, 2010, in corresponding European Patent Application No. 07706314.7.
* cited by examiner

*Primary Examiner* — Janet Andres
*Assistant Examiner* — Heidi Reese
(74) *Attorney, Agent, or Firm* — Buchanan Ingersoll & Rooney PC

(57) ABSTRACT

Disclosed is an improved process for producing nitroguanidine derivatives represented by the formula (3),

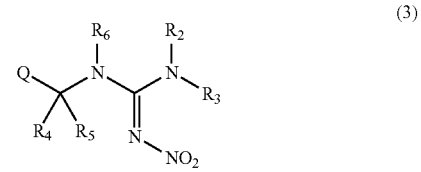

(3)

which has an insecticidal activity, or a salt thereof, wherein the substituents are defined herein, in which nitroisourea derivatives represented by the following general formula (1) or a salt thereof

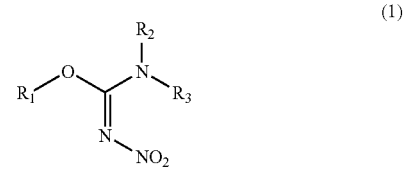

(1)

wherein the substituents are defined herein, and compounds represented by the following general formula (2) or a salt thereof, wherein the substituents are defined herein,

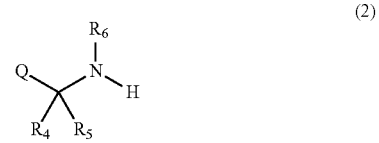

(2)

are reacted in the presence of a base in an aqueous solution wherein an inorganic salt is dissolved at not less than 50% of its saturated solubility.

2 Claims, No Drawings

PROCESS FOR PRODUCING NITROGUANIDINE DERIVATIVES

TECHNICAL FIELD

The present invention relates to an improved process for producing nitroguanidine derivatives having an insecticidal activity.

BACKGROUND ART

Nitroguanidine derivatives having an insecticidal activity and a process for producing the same have been disclosed in Japanese Patent Laid-open No. 1990-288860, Japanese Patent Laid-open No. 1991-157308, Japanese Patent Laid-open No. 1991-291267 and Japanese Patent Laid-open No. 1995-179448. However, for example, as typically described in Japanese Patent Laid-open No. 1995-179448 and the like, the problem occurs in the production method that exchange reactions between isothiourea derivatives and amines are frequent, thereby releasing mercaptans as by-products having a strong distasteful odor. As an alternative method, in Japanese Patent Laid-open No. 1998-120666, there has been a disclosed process for producing guanidine derivatives represented by the following general formula (B) having an insecticidal activity, in which isourea compounds represented by the following general formula (A) or a salt thereof and amines or a salt thereof are reacted,

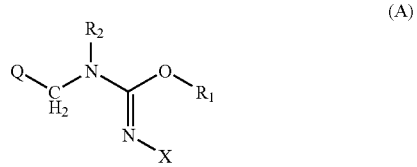

wherein, in the formula, $R_1$ represents a hydrocarbon group which may be substituted; $R_2$ represents hydrogen or a hydrocarbon group which may be substituted; Q represents a heterocyclic group which may be substituted; and X represents an electron-withdrawing group,

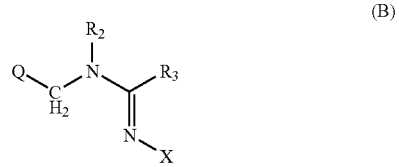

wherein, in the formula, $R_3$ represents an amino group which may be substituted; and $R_2$, Q and X represent the same as those described above.

However, according to this method, there is a problem in that expensive isourea compounds represented by the general formula (A) must be employed as intermediates in order to produce guanidine derivatives represented by the general formula (B) having an insecticidal activity, thus increasing the production cost.

As an alternative method, in Japanese Patent Laid-open No. 2000-103776, there has been disclosed a process for producing guanidine derivatives having an insecticidal activity, in which inexpensive nitroisourea derivatives or a salt thereof and amines or a salt thereof are reacted.

However, there were some problems to be solved for industrial application such that the stability of the nitroisourea derivatives are low, by-products are generated in large quantities in the reaction and the like.

Patent Document 1: Japanese Patent Laid-open No. 1990-288860
Patent Document 2: Japanese Patent Laid-open No. 1991-157308
Patent Document 3: Japanese Patent Laid-open No. 1991-291267
Patent Document 4: Japanese Patent Laid-open No. 1995-179448
Patent Document 5: Japanese Patent Laid-open No. 1998-120666
Patent Document 6: Japanese Patent Laid-open No. 2000-103776

DISCLOSURE OF THE INVENTION

An object of the present invention is to provide an industrially advantageous process for producing guanidine derivatives having an insecticidal activity, by overcoming the above problems in the prior art. That is, an object of the present invention is to provide an improved process for producing various guanidine derivatives having an insecticidal activity with high selectivity and in a high yield, while using inexpensive nitroisourea intermediates.

In order to achieve the above objects, the present inventors have conducted an extensive study of a process for producing nitroguanidine derivatives represented by the general formula (3) (hereinafter referred to as the compound (3) in some cases) or a salt thereof.

As a result, the present inventors have found a process for producing the aforementioned nitroguanidine derivatives represented by the following general formula (3), in which nitroisourea derivatives represented by the following general formula (1) (hereinafter referred to as the compound (1) in some cases) or a salt thereof and amines represented by the following general formula (2) (hereinafter referred to as the amine derivatives (2) in some cases) or a salt thereof are reacted in the presence of a base in an aqueous solution wherein an inorganic salt is dissolved at not less than 50% of its saturated solubility,

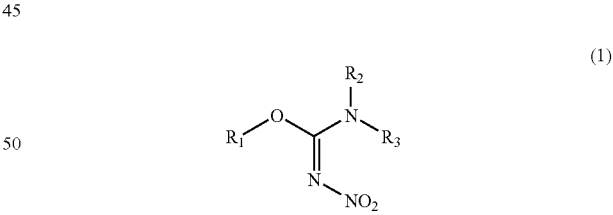

wherein, in the formula, $R_1$ represents an alkyl group having 1 to 4 carbon atoms or a benzyl group; $R_2$ represents an alkyl group having 1 to 4 carbon atoms; and $R_3$ represents a hydrogen atom or an alkyl group having 1 to 4 carbon atoms,

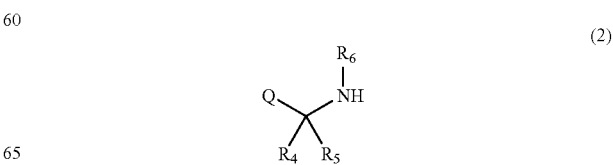

wherein, in the formula, $R_4$, $R_5$ and $R_6$ each independently represent a hydrogen atom or an alkyl group having 1 to 4 carbon atoms; and Q represents a 5- or 6-membered heterocyclic group which contains at least one each of a nitrogen atom, an oxygen atom and a sulfur atom and may be substituted with a halogen atom (The heterocyclic group herein represents a pyridyl group, a pyridine-N-oxide group, a pyrimidinyl group, a pyridazyl group, a furyl group, a tetrahydrofuryl group, a thienyl group, a tetrahydrothienyl group, a tetrahydropyranyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group or a tetrazolyl group.),

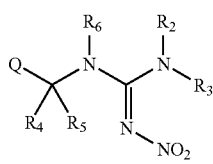

(3)

wherein, in the formula, $R_2$ represents an alkyl group having 1 to 4 carbon atoms; $R_3$, $R_4$, $R_5$ and $R_6$ each independently represent a hydrogen atom or an alkyl group having 1 to 4 carbon atoms; and Q represents a 5- or 6-membered heterocyclic group which contains at least one each of a nitrogen atom, an oxygen atom and a sulfur atom and may be substituted with a halogen atom (The heterocyclic group herein represents the same as those described above).

That is, the present invention relates to an industrially advantageous process for producing the compound (3) or a salt thereof, which makes it possible to suppress the decomposition of the compound (1) by reacting the compound (1) or a salt thereof with the amine derivatives (2) in an aqueous solution wherein an inorganic salt is dissolved at not less than 50% of its saturated solubility, and further to suppress the generation of by-products by adding a base.

In addition, in the present invention, the nitroisourea derivatives represented by the general formula (1) may contain nitroisourea derivatives having a double bond between the other nitrogen atom and carbon atom.

According to the method of the present invention, it is possible to obtain nitroguanidine derivatives having an excellent insecticidal activity with high selectivity and in a high yield, while using inexpensive nitroisourea derivatives, and it is possible to produce it in an industrially advantageous way.

BEST MODE FOR CARRYING OUT THE INVENTION

The process for producing nitroguanidine derivatives of the present invention or a salt thereof is a process for producing nitroguanidine derivatives represented by the following general formula (3) or a salt thereof, in which nitroisourea derivatives represented by the following general formula (1) or a salt thereof and compounds represented by the following general formula (2) or a salt thereof are reacted in the presence of a base in an aqueous solution wherein an inorganic salt is dissolved at not less than 50% of its saturated solubility,

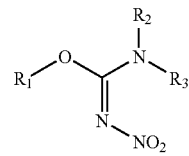

(1)

wherein, in the formula, $R_1$ represents an alkyl group having 1 to 4 carbon atoms or a benzyl group; $R_2$ represents an alkyl group having 1 to 4 carbon atoms; and $R_3$ represents a hydrogen atom or an alkyl group having 1 to 4 carbon atoms, (2)

wherein, in the formula, $R_4$, $R_5$ and $R_6$ each independently represent a hydrogen atom or an alkyl group having 1 to 4 carbon atoms; and Q represents a 5- or 6-membered heterocyclic group which contains at least one each of a nitrogen atom, an oxygen atom and a sulfur atom and may be substituted with a halogen atom (The heterocyclic group herein represents a pyridyl group, a pyridine-N-oxide group, a pyrimidinyl group, a pyridazyl group, a furyl group, a tetrahydrofuryl group, a thienyl group, a tetrahydrothienyl group, a tetrahydropyranyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group or a tetrazolyl group.),

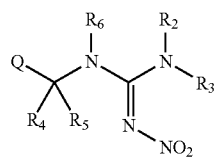

(3)

wherein, in the formula, $R_2$ represents an alkyl group having 1 to 4 carbon atoms; $R_3$, $R_4$, $R_5$ and $R_6$ each independently represent a hydrogen atom or an alkyl group having 1 to 4 carbon atoms; and Q represents a 5- or 6-membered heterocyclic group which contains at least one each of a nitrogen atom, an oxygen atom and a sulfur atom and may be substituted with a halogen atom (The heterocyclic group herein represents the same as those described above).

The method of the present invention makes it possible to suppress the decomposition of the starting material by carrying out the reaction in an aqueous solution wherein an inorganic salt is dissolved at not less than 50% of its saturated solubility, and further to suppress the generation of by-products such as nitroisourea derivatives represented by the following general formula (4) or the like by carrying out the reaction in the presence of a base,

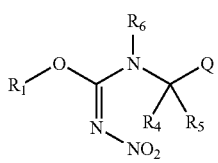
(4)

wherein, in the formula, $R_1$ represents an alkyl group having 1 to 4 carbon atoms; $R_4$, $R_5$ and $R_6$ each independently represent a hydrogen atom or an alkyl group having 1 to 4 carbon atoms; and Q represents a 5- or 6-membered heterocyclic group which contains at least one each of a nitrogen atom, an oxygen atom and a sulfur atom and may be substituted with a halogen atom (The heterocyclic group herein represents the same as those described above).

It is particularly important to suppress the generation of the nitroisourea derivatives of the general formula (4) because the nitroisourea derivatives are turned into nitroguanidine derivatives represented by the general formula (5) which is difficult to be removed, during the reaction,

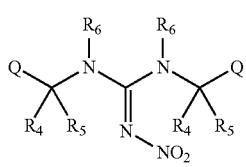
(5)

wherein, in the formula, $R_1$ represents an alkyl group having 1 to 4 carbon atoms; $R_4$, $R_5$ and $R_6$ each independently represent a hydrogen atom or an alkyl group having 1 to 4 carbon atoms; and Q represents a 5- or 6-membered heterocyclic group which contains at least one each of a nitrogen atom, an oxygen atom and a sulfur atom and may be substituted with a halogen atom (The heterocyclic group herein represents the same as those described above).

This enables the process of the present invention to obtain desired nitroguanidine derivatives or a salt thereof in a high yield as compared to the prior art, and at the same time to reduce a purification load. In this way, the production method of the present invention is excellent in the productivity, environmental sustainability and economical efficiency, and is useful as an industrial production method.

The salt of the compound (3), the compound (1) and the amine derivatives (2) may be a salt which can be industrially allowable, and examples thereof include salts of inorganic acids such as hydrochloric acid, hydrobromic acid, hydroiodic acid, phosphoric acid, sulfuric acid, perchloric acid and the like; and salts of organic acids such as formic acid, acetic acid, tartaric acid, malic acid, citric acid, oxalic acid, succinic acid, benzoic acid, picric acid, methanesulfonic acid, p-toluenesulfonic acid and the like. Of these salts, preferably used are hydrochloride and sulfate.

Specifically, the reaction can be performed in accordance with the following method. The amine derivatives (2) are known compounds, and can be produced, for example, by a method described in DE 3727126A, Japanese Patent Laid-open No. 1993-286936, Japanese Patent Laid-open No. 1995-179448, EP 446913A, Japanese Patent Laid-open No. 1992-21674 or the like.

The amine derivatives (2) or a salt thereof are used in an amount of from 0.8 to 10 mole equivalents and preferably from 0.9 to 1.5 mole equivalents, based on the compound (1) or a salt thereof. By carrying out the reaction within the above range, the generation of by-products can be effectively suppressed, and at the same time the reaction of the amine derivatives (2) or a salt thereof and the compound (1) or a salt thereof can be selectively carried out. Thus, the guanidine derivatives can be obtained in a high yield.

By carrying out the reaction in the presence of a base, side reaction with amino group can be suppressed and the reaction selectivity can be enhanced. As such a basic substance, there can be used, for example, inorganic bases such as alkali metal carbonate (such as sodium carbonate, potassium carbonate or the like), alkali metal hydroxide (such as sodium hydroxide, potassium hydroxide or the like), and alkaline earth metal hydroxide (such as calcium hydroxide or the like). In the present invention, one or more kinds of these substances can be selected and used. These bases can be properly selected in the range of 0.05 to 5 mole equivalents, based on the compound (1) and used.

By carrying out the reaction in suspension of the compound (1) and an aqueous solution wherein an inorganic salt is dissolved at not less than 50% of its saturated solubility, the decomposition of the compound (1) can be suppressed and the reaction yield can be enhanced. The amount of the inorganic salt can be properly selected in the range of 50 to 100% of its saturated solubility, but it is preferably selected in the range of 70 to 100% of its saturated solubility from the viewpoint of the above effects. Incidentally, the saturated solubility of the inorganic salt is a value at a water temperature at the time of the reaction of the compound (1) and the compound (2).

The inorganic salts reduce the solubility of the compound (1) and at the same time serves as a freezing mixture. It is considered that the reaction makes it possible to suppress the decomposition of the compound (1) and also to enhance the reaction selectivity when the initial reaction temperature is as low as possible. The present inventors have conducted an extensive study on the basis of such knowledge and as a result, have found that these effects can be achieved when the concentration of the inorganic salt is not less than 50% of its saturated solubility.

As such an inorganic salt, there can be used lithium salts such as lithium chloride, lithium bromide, lithium iodide, lithium nitrate, lithium sulfate and the like; sodium salts such as sodium chloride, sodium bromide, sodium iodide, sodium nitrate, sodium sulfate and the like; potassium salts such as potassium chloride, potassium bromide, potassium iodide, potassium nitrate, potassium sulfate, potassium phosphate and the like; magnesium salts such as magnesium chloride, magnesium bromide, magnesium iodide, magnesium nitrate, magnesium sulfate, magnesium phosphate and the like; and calcium salts such as calcium chloride, calcium bromide, calcium iodide, calcium nitrate, calcium sulfate, calcium phosphate and the like. In the present invention, one or more kinds of these salts can be selected and used.

The amount of the inorganic salt is properly selected in the range of 50 to 100% of its saturated solubility. Herein, the saturated solubility is defined as a relative value of the concentration of the inorganic salt that is actually dissolved on the assumption that the saturated solubility of inorganic salt in water is 100%. For example, since the concentration of a saturated sodium chloride solution at 20 degree centigrade is about 26.4 weight %, the saturated solubility of 50 to 100% of sodium chloride at 20 degree centigrade means a concentration of 13.2 to 26.4 weight %.

The reaction temperature is usually in the range of −30 to 100 degree centigrade and preferably in the range of −20 to 50 degree centigrade. The reaction time is usually in the range of 10 minutes to 50 hours and preferably in the range of 1 to 25 hours.

In the present invention, it is preferable that $R_1$ and $R_2$ are each independently an alkyl group having 1 to 4 carbon atoms, $R_3$ is a hydrogen atom, and $R_4$, $R_5$ and $R_6$ are each independently a hydrogen atom. Of these, Q is preferably a 2-chloro-5-thiazolyl group, a 2-chloro-5-pyridinyl group or a 3-tetrahydrofuranyl group because of its excellent insecticidal activity.

EXAMPLES

The present invention is now illustrated in detail below with reference to Examples and Comparative Examples. However, the present invention shall not be limited in any way by these Examples and Comparative Examples. The pH was measured with pH test paper unless otherwise described.

Comparative Example 1

Preparation of 1-methyl-2-nitro-3-[(3-tetrahydrofuryl)methyl]guanidine (Compound (3))

[(3-tetrahydrofuryl)methyl]amine (38.0 g, 0.38 mole) and 56.99 g of water were mixed, and the resulting mixture was cooled to 5 degree centigrade. Furthermore, 3.05 g (0.07 mole) of 1N NaOH was added to the solution, and then N,O-dimethyl-N'-nitroisourea (49.2 g, 0.37 mole) was introduced to the solution. The suspension was stirred at 5 degree centigrade for 4 hours, and then heated to 10 degree centigrade, and further stirred for 10 hours. 35% hydrochloric acid (6.7 g, 0.07 mole) was added to the suspension so that the pH became not more than 4. Water and acetonitrile were added to the above suspension for complete dissolution. The resulting solution was analyzed by HPLC and as a result, the reaction yield of the titled compound was 86%.

Comparative Example 2

Preparation of 1-methyl-2-nitro-3-[(3-tetrahydrofuryl)methyl]guanidine (Compound (3))

[(3-tetrahydrofuryl)methyl]amine (38.0 g, 0.38 mole), 31.3 g of sodium chloride and 125.0 g of water were mixed, and the resulting mixture was cooled to −10 degree centigrade. N,O-dimethyl-N'-nitroisourea (49.2 g, 0.37 mole) was introduced into the above solution. Sodium chloride was dissolved in water with 76% of the saturated solubility at a water temperature of −10 degree centigrade. The suspension was stirred at −10 degree centigrade for 4 hours and then heated to 10 degree centigrade, and further stirred for 19 hours. 35% hydrochloric acid (6.7 g, 0.07 mole) was added to the suspension so that the pH became not more than 4. Water and acetonitrile were added to the above suspension for complete dissolution. The resulting solution was analyzed by HPLC and as a result, the reaction yield of the titled compound was 88%.

Example 1

Preparation of 1-methyl-2-nitro-3-[(3-tetrahydrofuryl)methyl]guanidine (Compound (3))

[(3-tetrahydrofuryl)methyl]amine (38.0 g, 0.38 mole), 27.4 g of sodium chloride and 107.0 g of water were mixed, and the resulting mixture was cooled to −10 degree centigrade. Furthermore, 2.3 g (0.06 mole) of 96% NaOH was added to the solution and dissolved. Sodium chloride was dissolved in water with 78% of the saturated solubility at a water temperature of −10 degree centigrade. N,O-dimethyl-N'-nitroisourea (49.2 g, 0.37 mole) was introduced into the above solution, stirred at −10 degree centigrade for 4 hours, and then heated to 10 degree centigrade and further stirred for 19 hours. 35% hydrochloric acid (6.7 g, 0.07 mole) was added to the suspension so that the pH became not more than 4. Water and acetonitrile were added to the above suspension for complete dissolution. The resulting solution was analyzed by HPLC and as a result, the reaction yield of the titled compound was 95%.

Example 2

Preparation of 1-methyl-2-nitro-3-[(3-tetrahydrofuryl)methyl]guanidine (Compound (3))

14.0 g of sodium chloride and 53.8 g of water were mixed, and the resulting mixture was cooled to −10 degree centigrade. N,O-dimethyl-N'-nitroisourea (49.2 g, 0.37 mole) was introduced into the above solution, and 4.3 g (0.05 mole) of 48% NaOH was further added to the suspension and stirred. Thereafter, [(3-tetrahydrofuryl)methyl]amine (38.0 g, 0.38 mole) was introduced dropwise to the suspension. Sodium chloride was dissolved in water with 76% of the saturated solubility at a water temperature of −10 degree centigrade. The suspension was stirred at −10 degree centigrade for 4 hours and then heated to 20 degree centigrade, and further stirred for 6 hours. Then, 35% hydrochloric acid (8.5 g, 0.08 mole) was added to the suspension so that the pH became not more than 4. Water and acetonitrile were added to the above suspension for complete dissolution. The resulting solution was analyzed by HPLC and as a result, the reaction yield of the titled compound was 96%.

Example 3

Preparation of 1-methyl-2-nitro-3-[(3-tetrahydrofuryl)methyl]guanidine (Compound (3))

[(3-tetrahydrofuryl)methyl]amine (43.3 g, 0.43 mole), 31.3 g of sodium chloride and 125 g of water were mixed, and the resulting mixture was cooled to −10 degree centigrade. Furthermore, 2.9 g (0.07 mole) of 96% NaOH was added to the solution and dissolved. Sodium chloride was dissolved in water with 76% of the saturated solubility at a water temperature of −10 degree centigrade. N,O-dimethyl-N'-nitroisourea (49.2 g, 0.37 mole) was introduced into the above solution, stirred at −10 degree centigrade for 4 hours, and then heated to 0 degree centigrade and further stirred for 18 hours. 35% hydrochloric acid (13.1 g, 0.13 mole) was added to the suspension so that the pH became not more than 4. The suspension was heated and dissolved for carrying out recrystallization. The precipitated crystal was filtered, and the filtered crystal was washed with cold water and then dried. 61 g of a 1-methyl-2-nitro-3-[(3-tetrahydrofuryl)methyl]guanidine with a purity of 99% was obtained. The isolated yield at this time was 81%.

$^1$H-NMR (CDCl$_3$, ppm): 1.62-1.71 (1H, m), 2.05-2.16 (1H, m), 2.58-2.67 (1H, m), 2.97 (3H, d, J=5.3 Hz), 3.36 (2H, br-t), 3.62-3.66 (1H, m), 3.71-3.84 (2H, m), 3.89-3.95 (1H, m), 6.04 (1H, br-s), 9.35 (1H, br-s)

Example 4

Preparation of 1-[(2-chloro-5-pyridyl)methyl]-3-methyl-2-nitroguanidine (Compound (3))

1.3 g of sodium chloride and 4.65 g of water were mixed, and the resulting mixture was cooled to −10 degree centigrade. N,O-dimethyl-N'-nitrosourea (4.5 g, 0.03 mole) was introduced into the above solution, and 0.58 g (4.64 mmole) of 32% NaOH was further added to the suspension and stirred. Thereafter, [(2-chloro-5-pyridyl)methyl]amine (4.93 g, 0.03 mole) was introduced dropwise to the suspension. Sodium chloride was dissolved in water with 78% of the saturated solubility at a water temperature of −10 degree centigrade. The solution was stirred at −10 degree centigrade for 4 hours and then heated to 20 degree centigrade, and further stirred for 6 hours. Then, 35% hydrochloric acid (0.7 g, 6.71 mmole) was added to the suspension so that the pH became not more than 4. The resulting solution was extracted with ethyl acetate and concentrated under a reduced pressure, and then recrystallized. Thus, 6.5 g of a 1-[(2-chloro-5-pyridyl)methyl]-3-methyl-2-nitroguanidine was obtained. The isolated yield at this time was 81%.

$^1$H-NMR (DMSO-d6, ppm): 2.85 (3H, br-s), 4.44 (2H, d, J=5.4 Hz), 7.51 (1H, d, J=8.3 Hz), 7.72 (1H, br-s), 7.80 (1H, dd, J=8.3, 2.4 Hz), 8.37 (1H, d, J=2.4 Hz), 9.19 (1H, br-s)

Example 5

Preparation of 1-methyl-2-nitro-3-[3-tetrahydrofuryl)methyl]guanidine Compound (3))

18.75 g of sodium chloride, 115.0 g of water, 3.01 g (0.07 mole) of 96% NaOH and [(3-tetrahydrofuryl)methyl]amine (39.9 g, 0.39 mole) were mixed, and the resulting mixture was cooled to −10 degree centigrade. N,O-dimethyl-N'-nitrosourea (49.2 g, 0.37 mole) was introduced into the above solution. Sodium chloride was dissolved in water with 53% of the saturated solubility at a water temperature of −10 degree centigrade. The solution was stirred at −10 degree centigrade for 4 hours, heated to 0 degree centigrade, and further stirred for 19 hours. Then, 35% hydrochloric acid (13.1 g, 0.13 mole) was added to the suspension so that the pH became not more than 4. The suspension was heated and dissolved for carrying out recrystallization. The precipitated crystal was filtered, and the filtered crystal was washed with cold water and then dried. 59 g of a 1-methyl-2-nitro-3-[(3-tetrahydrofuryl)methyl]guanidine with a purity of 99% was obtained. The isolated yield at this time was 78%.

Comparative Example 3

To a solution obtained by mixing 7.2 g of sodium chloride and 53.8 g of water was added N,O-dimethyl-N'-nitrosourea (49.2 g, 0.37 mole). The above suspension was cooled to −10 degree centigrade and as a result, it was solidified. In addition, sodium chloride was dissolved in water with 45% of the saturated solubility at a water temperature of −10 degree centigrade.

Comparative Example 4

To a solution of 1.0 g of N,O-dimethyl-N'-nitrosourea and 10 ml of methanol was added 0.91 g of [(3-tetrahydrofuryl)methyl]amine, and the resulting mixture was stirred at room temperature for 3 hours. Then, an aqueous hydrochloric acid solution (4M) was added to the solution and subsequently extracted with ethyl acetate.

In Comparative Example 2, 2-nitro-1,3-bis(tetrahydro-3-furylmethyl)guanidine of a by-product was generated in an amount of 5 mole %, based on 100 mole % of the starting material, which was difficult to be removed. On the other hand, since the reaction highly selectively proceeded in a high yield by the method described in Example 2, the amount of 2-nitro-1,3-bis(tetrahydro-3-furylmethyl)guanidine as a by-product was less than 1 mole %, thus greatly reducing the amount of the by-product. That is, according to the present invention, it is possible to reduce the load when the desired compound of 1-methyl-2-nitro-3-(tetrahydro-3-furylmethyl)guanidine is purified. Thus, the method is useful as an industrial production method.

The invention claimed is:

1. A process for producing nitroguanidine derivatives represented by the following general formula (3) or a salt thereof, in which nitroisourea derivatives represented by the following general formula (1) or a salt thereof and compounds represented by the following general formula (2) or a salt thereof are reacted in the presence of a base in an aqueous solution wherein an inorganic salt is dissolved at not less than 50% of its saturated solubility,

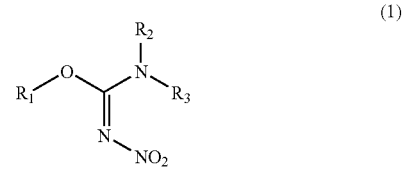

(1)

wherein, in the formula, $R_1$ represents an alkyl group having 1 to 4 carbon atoms; $R_2$ represents an alkyl group having 1 to 4 carbon atoms; and $R_3$ represents a hydrogen atom,

(2)

wherein, in the formula, $R_4$, $R_5$ and $R_6$ represent a hydrogen atom; and Q represents a pyridyl group which may be substituted with a halogen atom, a thiazolyl group which may be substituted with a halogen atom, or a tetrahydrofuryl group,

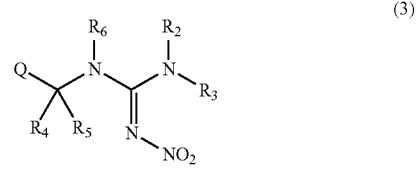

(3)

wherein, in the formula, $R_2$ represents an alkyl group having 1 to 4 carbon atoms; $R_3$, $R_4$, $R_5$ and $R_6$ represent a hydrogen atom; and Q represents a pyridyl group which may be substituted with a halogen atom, a thiazolyl group which may be substituted with a halogen atom, or a tetrahydrofuryl group.

2. The process for producing nitroguanidine derivatives as set forth in claim 1, in which $R_2$ is a methyl group, and Q is a tetrahydrofuryl group.

* * * * *